United States Patent
Suzuki et al.

(10) Patent No.: US 10,088,659 B2
(45) Date of Patent: Oct. 2, 2018

(54) SAMPLE RETAINING MEMBER INSERTION-REMOVAL MECHANISM AND IMAGE ACQUISITION DEVICE

(71) Applicant: HAMAMATSU PHOTONICS K.K., Hamamatsu-shi, Shizuoka (JP)

(72) Inventors: Yasumoto Suzuki, Hamamatsu (JP); Satoshi Watanabe, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 270 days.

(21) Appl. No.: 14/897,015

(22) PCT Filed: Mar. 25, 2014

(86) PCT No.: PCT/JP2014/058329
§ 371 (c)(1),
(2) Date: Dec. 9, 2015

(87) PCT Pub. No.: WO2014/199696
PCT Pub. Date: Dec. 18, 2014

(65) Prior Publication Data
US 2016/0124204 A1    May 5, 2016

(30) Foreign Application Priority Data

Jun. 12, 2013   (JP) ................ 2013-123930

(51) Int. Cl.
*G02B 21/26* (2006.01)
*G02B 21/36* (2006.01)
(Continued)

(52) U.S. Cl.
CPC ....... *G02B 21/26* (2013.01); *G01N 35/00029* (2013.01); *G02B 21/34* (2013.01); *G02B 21/36* (2013.01); *G01N 2035/00039* (2013.01)

(58) Field of Classification Search
CPC ............... G02B 21/0088; G02B 21/24; G02B 21/26–21/30; G02B 21/32; G02B 21/34;
(Continued)

(56) References Cited

U.S. PATENT DOCUMENTS

| 5,659,421 A | 8/1997 | Rahmel et al. |
| 5,948,359 A * | 9/1999 | Kalra ..................... G01N 1/312 422/510 |

(Continued)

FOREIGN PATENT DOCUMENTS

| CN | 102004044 | 4/2011 |
| EP | 1207392 | 5/2002 |

(Continued)

OTHER PUBLICATIONS

International Preliminary Report on Patentability dated Dec. 23, 2015 for PCT/JP2014/058329.

*Primary Examiner* — Stephone B Allen
*Assistant Examiner* — James McGee
(74) *Attorney, Agent, or Firm* — Drinker Biddle & Reath LLP

(57) ABSTRACT

A sample retaining member insertion-removal mechanism is configured so that a receiver is driven to an advance position by a receiver driving unit to project out through an opening of a stage so that a receiving surface makes a downward slope toward a receiving surface positioning portion. Because of this, the sample retaining member insertion-removal mechanism can position the sample retaining member by the receiving surface positioning portion through the use of the downward slope of the receiving surface by simply placing the sample retaining member on the receiving surface. After the positioning by the receiving surface positioning portion, the receiver is driven to a retraction position by the receiver driving unit, whereby the sample retaining member is transferred from the receiver to the stage.

7 Claims, 11 Drawing Sheets

(51) Int. Cl.
*G02B 21/34* (2006.01)
*G01N 35/00* (2006.01)

(58) Field of Classification Search
CPC ... G01N 35/00029; G01N 2035/00039; G01N 2035/00049
USPC .......................................... 359/363, 391–398
See application file for complete search history.

(56) References Cited

U.S. PATENT DOCUMENTS

| | | |
|---|---|---|
| 2002/0061261 A1 | 5/2002 | Pfeifer et al. |
| 2010/0128944 A1 | 5/2010 | Zahniser et al. |
| 2010/0135861 A1 | 6/2010 | Sage et al. |
| 2011/0048142 A1 | 3/2011 | Pfeifer |
| 2011/0249327 A1 | 10/2011 | Yamamoto et al. |
| 2012/0267440 A1 | 10/2012 | Nakaya et al. |
| 2015/0205089 A1* | 7/2015 | Machida ............... G01N 1/312 359/391 |

FOREIGN PATENT DOCUMENTS

| | | |
|---|---|---|
| JP | S52-143848 A | 11/1977 |
| JP | H1-100508 | 4/1989 |
| JP | H08-320430 A | 12/1996 |
| JP | 2004-061942 A | 2/2004 |
| JP | 2007-065180 A | 3/2007 |
| JP | 2009-545782 A | 12/2009 |
| JP | 2012-013954 A | 1/2012 |

* cited by examiner

SAMPLE RETAINING MEMBER INSERTION-REMOVAL MECHANISM AND IMAGE ACQUISITION DEVICE

TECHNICAL FIELD

The present invention relates to a sample retaining member insertion-removal mechanism and an image acquisition device.

BACKGROUND ART

As a conventional image acquisition device, there is, for example, the device described in Patent Literature 1. In this device, light from a specimen is split into two beams by a half prism and the beams are received by a photoelectric conversion element consisting of a two-dimensional imaging element such as a CCD area sensor. A control circuit for the photoelectric conversion element has a scan area setting unit capable of setting two arbitrary scan areas for two-dimensional scanning on a light receiving surface. Then, focusing control is executed based on a focus deviation signal obtained from beams received in the two scan areas set by the scan area setting unit and an entire or partial image of the specimen is taken.

CITATION LIST

Patent Literature

Patent Literature 1: Japanese Unexamined Patent Publication No. H8-320430

SUMMARY OF INVENTION

Technical Problem

In the image acquisition device as described above, a sample as the specimen is inserted into and removed from the device, for example, while being retained in a sample retaining member such as slide glass or microchip. When the sample retaining member is inserted into the device, it is necessary to position it relative to a stage; for this reason, to manually perform the positioning of the sample retaining member each time of insertion is burdensome and it may also be difficult to ensure positioning accuracy.

The present invention has been accomplished in order to solve the above problem and it is an object of the present invention to provide a sample retaining member insertion-removal mechanism capable of readily arranging a sample retaining member, while ensuring the positioning accuracy, and an image acquisition device using the same.

Solution to Problem

In order to solve the above problem, a sample retaining member insertion-removal mechanism according to the present invention is an insertion-removal mechanism for a sample retaining member to be used in an image acquisition device for acquiring an image of a sample, comprising: a stage having a mount surface for the sample retaining member to be mounted thereon, and an opening provided in the mount surface corresponding to a retaining region of the sample in the sample retaining member; a stage driving unit for driving the stage between an insertion-removal position of the sample retaining member and an image acquisition position of the sample; a receiver arranged at the insertion-removal position and having a receiving surface for the sample retaining member and a receiving surface positioning portion for setting a position of the sample retaining member on the receiving surface; and a receiver driving unit for driving the receiver between an advance position where the receiving surface projects out through the opening so as to make a downward slope toward the receiving surface positioning portion and a retraction position where the receiving surface is retracted from the opening.

This sample retaining member insertion-removal mechanism is configured so that at the insertion-removal position of the sample retaining member the receiver is driven to the advance position by the receiver driving unit to project out through the opening of the stage so that the receiving surface makes the downward slope toward the receiving surface positioning portion. Because of this, this sample retaining member insertion-removal mechanism can position the sample retaining member by the receiving surface positioning portion through the use of the downward slope of the receiving surface by simply placing the sample retaining member on the receiving surface, without need for positioning the sample retaining member by hand work. After the positioning by the receiving surface positioning portion, the receiver is driven to the retraction position by the receiver driving unit, whereby the sample retaining member is transferred from the receiver to the stage so that the sample retaining member can be readily and accurately arranged on the mount surface of the stage.

Preferably, the receiver driving unit drives the receiver to the advance position in conjunction with movement of the stage from the image acquisition position to the insertion-removal position by the stage driving unit. In this case, convenience of the insertion-removal mechanism can be improved.

Preferably, the stage further has a mount surface positioning portion for setting a position of the sample retaining member on the mount surface, and the mount surface positioning portion has a taper portion widening to the end when viewed from the mount surface. This allows the positioning on the mount surface of the stage to be readily carried out. Since the mount surface positioning portion has the taper portion, easiness of transfer can be ensured in transferring the sample retaining member from the receiver to the stage.

Preferably, the stage further has a clamp portion for butting the sample retaining member against the mount surface positioning portion in conjunction with movement of the stage from the insertion-removal position to the image acquisition position by the stage driving unit. This can prevent the sample retaining member from suffering positional deviation during the movement of the stage to the image acquisition position.

Preferably, an insertion-removal port for the sample retaining member is provided corresponding to the receiver, and a wall portion forming the insertion-removal port has a taper portion spreading out from the far side to the near side of the insertion-removal port. This can improve workability in putting the sample retaining member onto the receiver or in removing the sample retaining member from the receiver, through the insertion-removal port.

Preferably, when the receiver is moved to the advance position, a clearance larger than a thickness of the sample retaining member is present between the receiving surface and the wall portion forming the insertion-removal port. This can further improve the workability in putting the sample retaining member onto the receiver or in removing the sample retaining member from the receiver, through the insertion-removal port.

An image acquisition device according to the present invention comprises: the foregoing sample retaining member insertion-removal mechanism; a light source for applying light to the retaining region of the sample in the sample retaining member through the opening, when the stage is moved to the image acquisition position; and an imaging device for imaging a light figure of the sample formed by the light source.

This image acquisition device is configured so that at the insertion-removal position of the sample retaining member the receiver is driven to the advance position by the receiver driving unit to project out through the opening so that the receiving surface makes the downward slope toward the receiving surface positioning portion. Because of this, this image acquisition device can position the sample retaining member by the receiving surface positioning portion through the use of the downward slope of the receiving surface by simply placing the sample retaining member on the receiving surface, without need for positioning the sample retaining member by hand work. After the positioning by the receiving surface positioning portion, the receiver is driven to the retraction position by the receiver driving unit, whereby the sample retaining member is transferred from the receiver to the stage so that the sample retaining member can be readily and accurately arranged on the mount surface of the stage.

Advantageous Effects of Invention

The present invention has enabled the sample retaining member to be readily arranged, while ensuring the positioning accuracy.

DESCRIPTION OF EMBODIMENTS

Preferred embodiments of the sample retaining member insertion-removal mechanism and the image acquisition device according to the present invention will be described below in detail with reference to the drawings.

Figure 1:
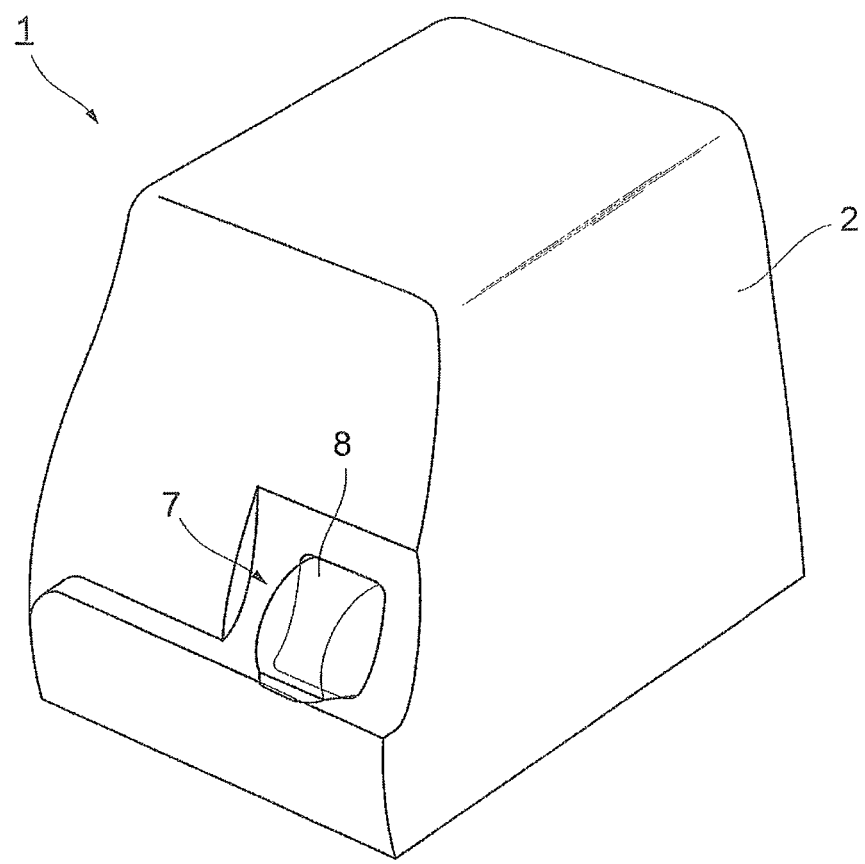
FIG. 1 is a perspective view showing external appearance of an image acquisition device configured with an insertion-removal mechanism for a sample retaining member according to an embodiment of the present invention.
Figure 2:
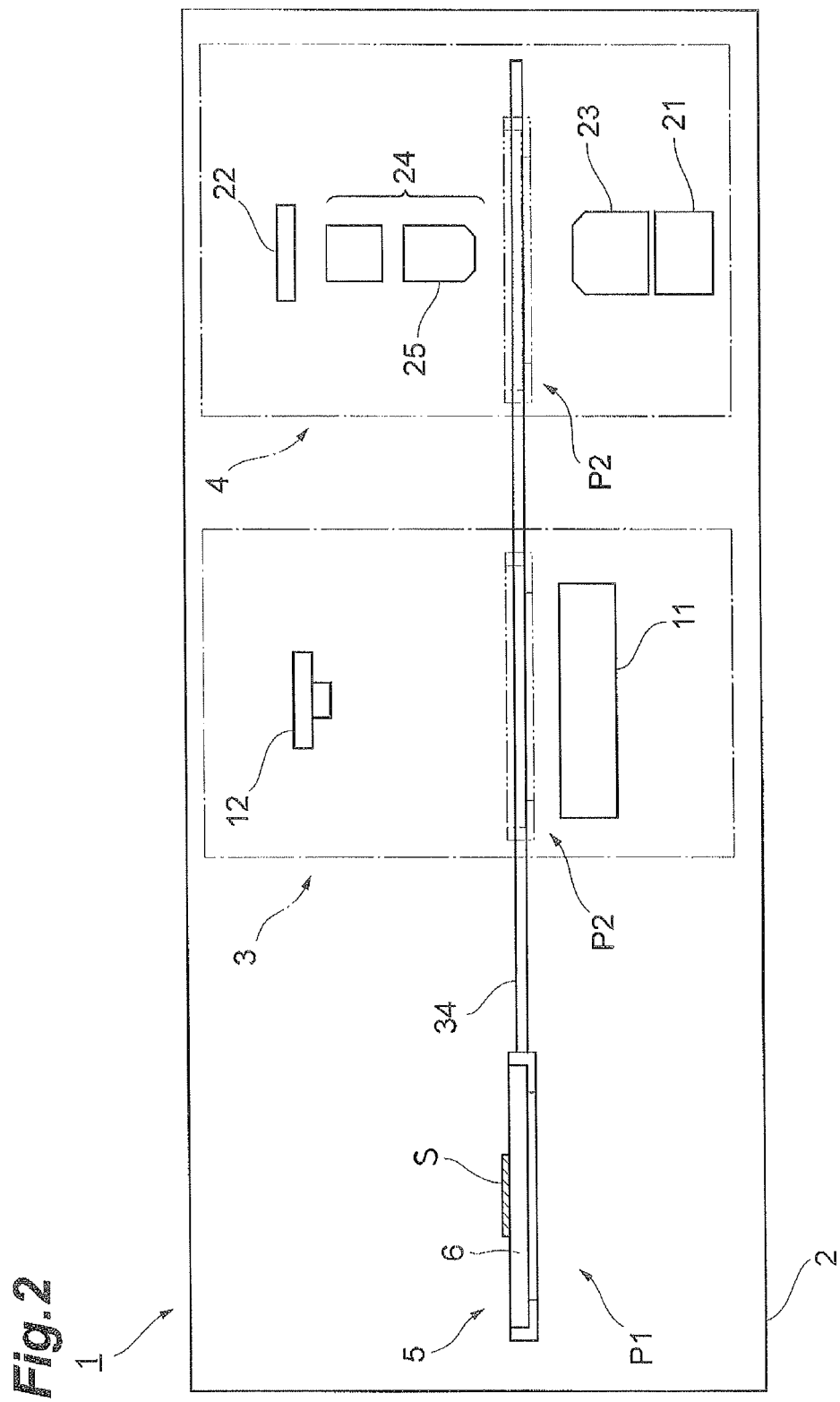
FIG. 2 is a schematic view showing an internal configuration of the image acquisition device.

FIG. 1 is a perspective view showing external appearance of an image acquisition device configured with an insertion-removal mechanism for a sample retaining member according to an embodiment of the present invention. FIG. 2 is a schematic view showing an internal configuration of the image acquisition device. As shown in FIGS. 1 and 2, the image acquisition device 1 has a macro image acquisition device 3 for acquiring a macro image of a sample S, a micro image acquisition device 4 for acquiring a micro image of the sample S, and a stage 5 movable between the macro image acquisition device 3 and the micro image acquisition device 4, housed in a housing 2 of a box shape. The image acquisition device 1 is a device that sets, for example, a plurality of linear divided regions in the macro image acquired by the macro image acquisition device 3, acquires images of the respective divided regions at a high magnification by the micro image acquisition device 4, and combines them to generate a virtual slide image.

The sample S to be observed by the image acquisition device 1 is, for example, a biological sample such as tissue cell. One sample S is inserted into the image acquisition device 1 every image acquisition, for example, in a state in which it is hermetically enclosed in a sample retaining member 6 (cf. FIG. 2) such as a glass slide. On the front side of the housing 2, as shown in FIG. 1, there is an insertion-removal portion 7 provided for inserting and removing the sample retaining member 6 into and from the image acquisition device 1. An open/close lid 8 is attached to the insertion-removal portion 7 and is configured to manually or automatically open and close in conjunction with insertion and removal of the sample retaining member 6. A below-described insertion-removal mechanism 30 (cf. FIG. 3) for the sample retaining member is provided corresponding to the insertion-removal portion 7, inside the image acquisition device 1 to support insertion of the sample retaining member 6 into the image acquisition device 1 and removal of the sample retaining member 6 from the image acquisition device 1.

The macro image acquisition device 3, as shown in FIG. 2, is configured including a light source 11 arranged on the bottom side of the stage 5 and an imaging device 12 arranged on the top side of the stage 5. The light source 11 to be used herein is, for example, a laser diode (LD), a light emitting diode (LED), a super luminescent diode (SLD), or a lamp type light source such as a halogen lamp. Light emitted from the light source 11 travels through an opening 42 (described later) of the stage 5 to be applied to the sample S retained in the sample retaining member 6. The imaging device 12 is, for example, an area image sensor capable of acquiring a two-dimensional image. The imaging device 12 acquires an entire image of a light figure of the sample S formed by the light source 11.

The micro image acquisition device 4 is configured including a light source 21 arranged on the bottom side of the stage 5 and an imaging device 22 arranged on the top side of the stage 5 as the macro image acquisition device 3 is. Light emitted from the light source 21 travels through the opening 42 of the stage 5 to be applied to the sample S retained in the sample retaining member 6. The imaging device 22 is composed, for example, of a two-dimensional imaging device such as a CMOS image sensor. The imaging device 22 sequentially acquires images of partial regions of a light figure of the sample S formed by the light source 21, for the respective divided regions.

The micro image acquisition device 4 has an illumination optical system. 23 arranged between the light source 21 and the stage 5 and an imaging optical system 24 arranged between the stage 5 and the imaging device 22. The imaging optical system 24 includes an objective 25 arranged opposite to the sample S. The objective 25 is provided with a motor or actuator such as a stepping motor (pulse motor) or piezoelectric actuator for driving the objective 25 in directions perpendicular to the stage 5. The focus position of imaging in acquisition of images of the sample S can be adjusted by changing the position of the objective 25 by these driving means.

The insertion-removal mechanism 30 for the sample retaining member will be described below in detail.

Figure 3:
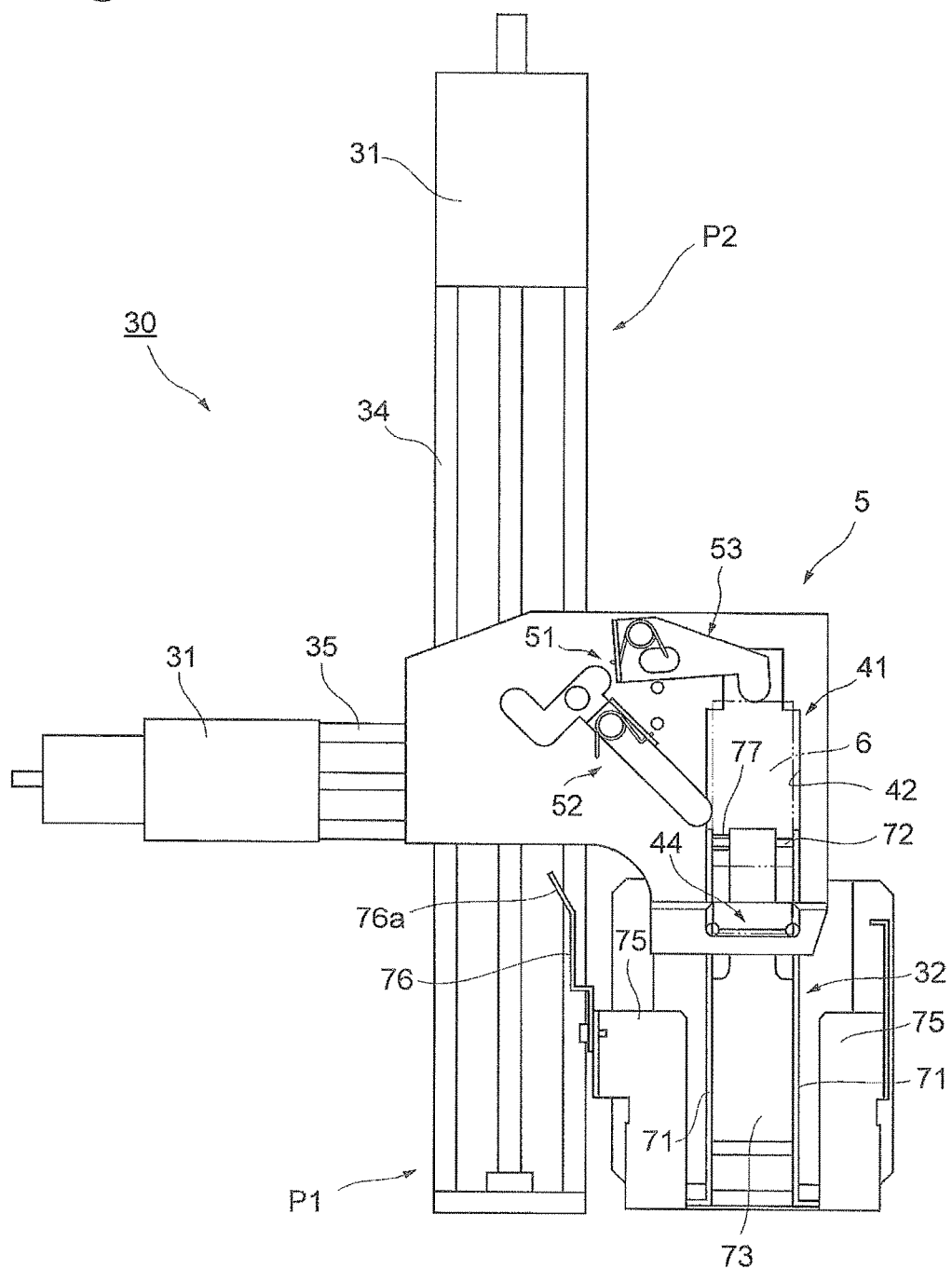
FIG. 3 is a plan view showing a configuration of the insertion-removal mechanism for the sample retaining member.

FIG. 3 is a plan view showing the configuration of the insertion-removal mechanism for the sample retaining member. As shown in the same figure, the insertion-removal mechanism 30 for the sample retaining member is configured including the aforementioned stage 5, stage driving units 31 for driving the stage 5, a receiver 32 arranged corresponding to the insertion-removal portion 7, and a receiver driving unit 33 (cf. FIG. 6) for driving the receiver 32.

The stage 5 has a first slider 34 extending from the receiver 32 side to the macro image acquisition device 3 and micro image acquisition device 4 side, and a second slider 35 extending perpendicularly to the first slider 34. The stage 5 is attached to the second slider 35 so as to be slidable thereon and the second slider 35 is attached to the first slider 34 so as to be slidable thereon.

The stage driving units 31 are composed, for example, of motors or actuators such as stepping motors (pulse motors) or piezoelectric actuators and are provided respectively for the first slider 34 and for the second slider 35. By the stage driving unit 31 provided for the first slider 34, the stage 5 is driven between an insertion-removal position (position corresponding to the receiver 32) P1 of the sample retaining member 6 and an image acquisition position (position corresponding to the macro image acquisition device 3 or position corresponding to the micro image acquisition device 4) P2 of the sample S. By the stage driving unit 31 provided for the second slider 35, the stage 5 is driven along the second slider 35. Movement of the stage 5 along the second slider 35 is used, for example, for movement of the field position of the objective 25 relative to the sample S in the micro image acquisition device 4.

Figure 4:
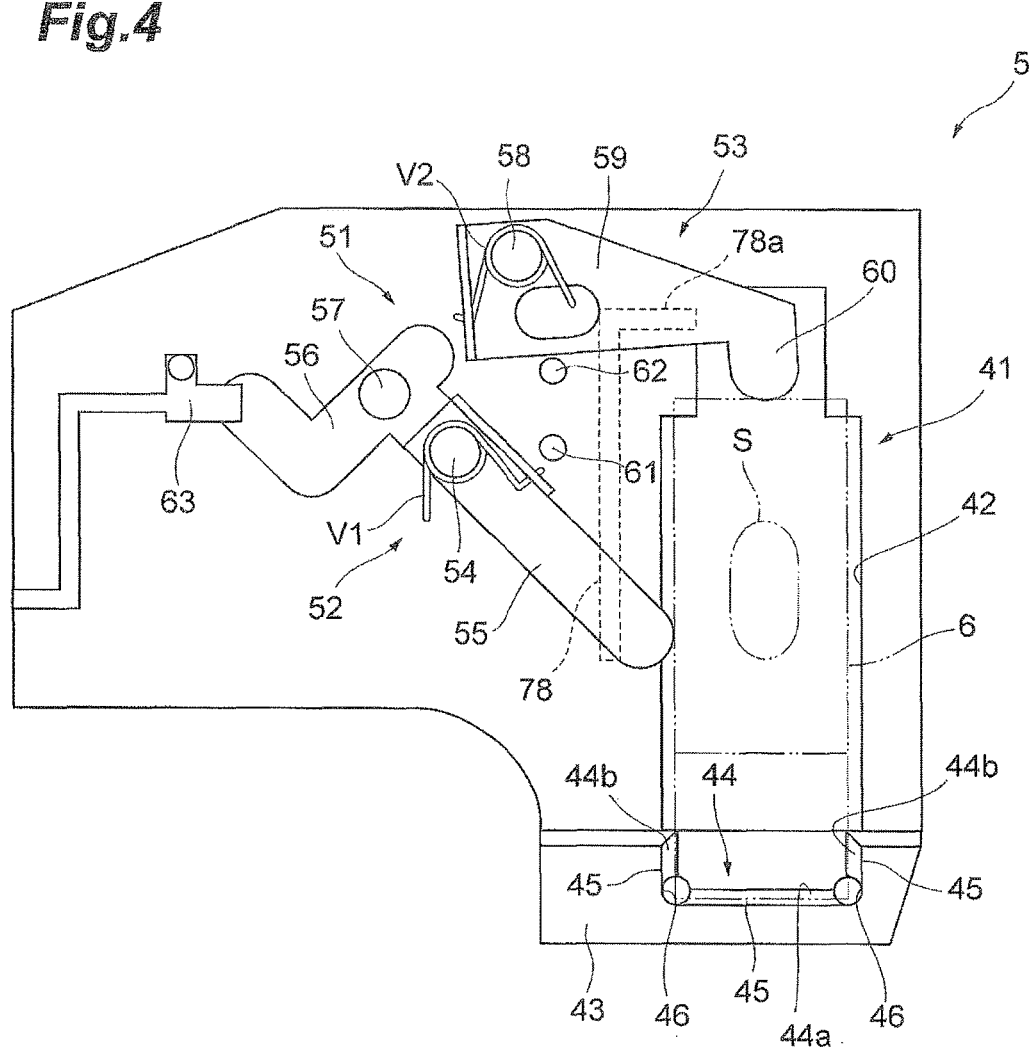
FIG. 4 is an enlarged plan view showing a configuration of a stage.

FIG. 4 is an enlarged plan view showing the configuration of the stage. As shown in the same figure, the stage 5 is provided with a mount surface 41 on which the sample retaining member 6 is to be mounted, and the opening 42 which is provided in the mount surface 41, corresponding to a retaining region of the sample S in the sample retaining member 6, so as not to overlap the first slider 34 and the second slider 35. The opening 42 opens in an approximately rectangular shape with the width slightly larger than the width of the sample retaining member 6.

In the stage 5, a thick portion 43 with the thickness a step larger is provided on a longitudinal one end side of the opening 42 (or on the near side when viewed from the insertion-removal portion 7). The thick portion 43 is cut in a rectangular shape so as to open on the opening 42 side in the width approximately equal to that of the sample retaining member 6, and the cut part has the same thickness as the other part of the stage 5. By such cutting of the thick portion 43, a mount surface positioning portion 44 is formed as a portion for supporting one end side of the sample retaining member 6 and setting the position of the sample retaining member 6 on the mount surface 41.

The mount surface positioning portion 44 has a wall portion 44a against which the longitudinal one end side of the sample retaining member 6 is to be butted, and wall portions 44b, 44b to extend along the lateral two edges of the sample retaining member 6. In the upper parts of these wall portions 44a, 44b, a taper portion 45 is formed so as to widen to the end when viewed from the mount surface 41 side. In the mount surface positioning portion 44, holes 46 with a circular cross section are formed so as to penetrate in the thickness direction of the stage 5, at positions where corners of the sample retaining member 6 are to be located. The holes 46 function to prevent the corners of the sample retaining member 6 from striking the wall portions 44a, 44b upon butting of the longitudinal one end side of the sample retaining member 6, thereby protecting the sample retaining member 6. On the other hand, on the longitudinal other end side of the opening 42 (the far side when viewed from the insertion-removal portion 7), the width of the opening is smaller than the width of the sample retaining member 6 on the far side with respect to a position corresponding to the corners of the sample retaining member 6. Because of this, the sample retaining member 6 is supported at its corners only, on the other end side thereof.

The stage 5 is provided with a clamp portion 51 for holding the sample retaining member 6 mounted on the mount surface 41. The clamp portion 51 has a long-side clamp 52 for supporting one end side (long side) in the width direction of the sample retaining member 6, and a short-side clamp 53 for supporting the other end side (short side) in the longitudinal direction of the sample retaining member 6.

The long-side clamp 52 is disposed so as to be rotatable around a rotary shaft 54 on the stage 5 and is biased, for example, counterclockwise by a spring V1. The long-side clamp 52 has a first portion 55 of a linear shape extending from the rotary shaft 54 toward the mount surface 41, and a second portion 56 of an approximate L-shape extending toward the opposite side to the first portion 55 with respect to the rotary shaft 54. A pin 57 projecting upward is provided on the base end side of the second portion 56. The short-side clamp 53 is disposed so as to be rotatable around a rotary shaft 58 on the stage 5 and is biased, for example, clockwise by a spring V2. The short-side clamp 53 has a first portion 59 of an approximate trapezoid shape to which the rotary shaft 58 is attached, and a second portion 60 of a linear shape as bent at an approximately right angle from the tip of the first portion 59.

When the stage 5 is located at the insertion-removal position P1 of the sample retaining member 6, a tip portion 76a (cf. FIG. 5) of a lever member 76 of the below-described receiver 32 is in contact with the pin 57 in the clamp portion 51. This contact rotates the long-side clamp 52 clockwise against a biasing force of the spring V1, so as to release the support of the long side of the sample retaining member 6 by the first portion 55 of the long-side clamp 52. Furthermore, the clockwise rotation of the long-side clamp 52 brings the base end side of the second portion 56 of the long-side clamp 52 into contact with the base end side of the first portion 59 of the short-side clamp 53. This contact results in rotating the short-side clamp 53 counterclockwise against a biasing force of the spring V2, so as to release the support of the short side of the sample retaining member 6 by the second portion 60 of the short-side clamp 53.

As the stage 5 moves from the insertion-removal position P1 of the sample retaining member 6 toward the image acquisition position P2, the contact state between the lever member 76 and the pin 57 becomes released in the clamp portion 51. This release results in rotating the long-side clamp 52 counterclockwise by the biasing force of the spring V1, so as to support the long side of the sample retaining member 6 by the first portion 55 of the long-side clamp 52. Furthermore, the counterclockwise rotation of the long-side clamp 52 releases the contact state between the base end side of the second portion 56 of the long-side clamp 52 and the base end side of the first portion 59 of the short-side clamp 53. This release results in rotating the short-side clamp 53 clockwise by the biasing force of the spring V2, so as to support the short side of the sample retaining member 6 by the second portion 60 of the short-side clamp 53. Therefore, the sample retaining member 6 on the mount surface 41 becomes held by the clamp portion 51 while butted against the mount surface positioning portion 44.

When the sample retaining member 6 is not mounted on the mount surface 41, the counterclockwise rotation of the long-side clamp 52 and the clockwise rotation of the short-side clamp 53 are regulated near the holding position of the sample retaining member 6 by regulation pins 61, 62. Arranged on the stage 5 is a contact sensor 63 which comes into contact with the tip end side of the second portion 56 of the long-side clamp 52 when the long-side clamp 52 is rotated counterclockwise by the biasing force of the spring V1. The contact sensor 63 allows the image acquisition device 1 side to figure out whether the sample retaining member 6 is held by the clamp portion 51.

Figure 5:
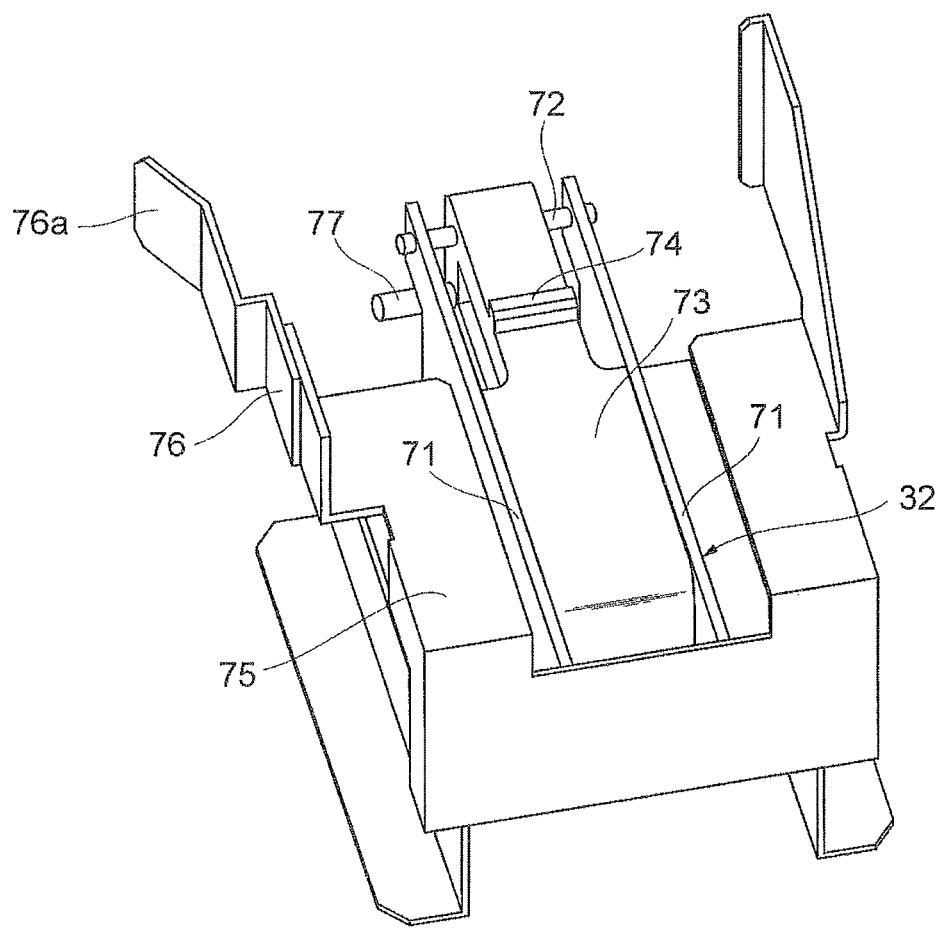
FIG. 5 is a perspective view showing a configuration of a receiver.
Figure 6:
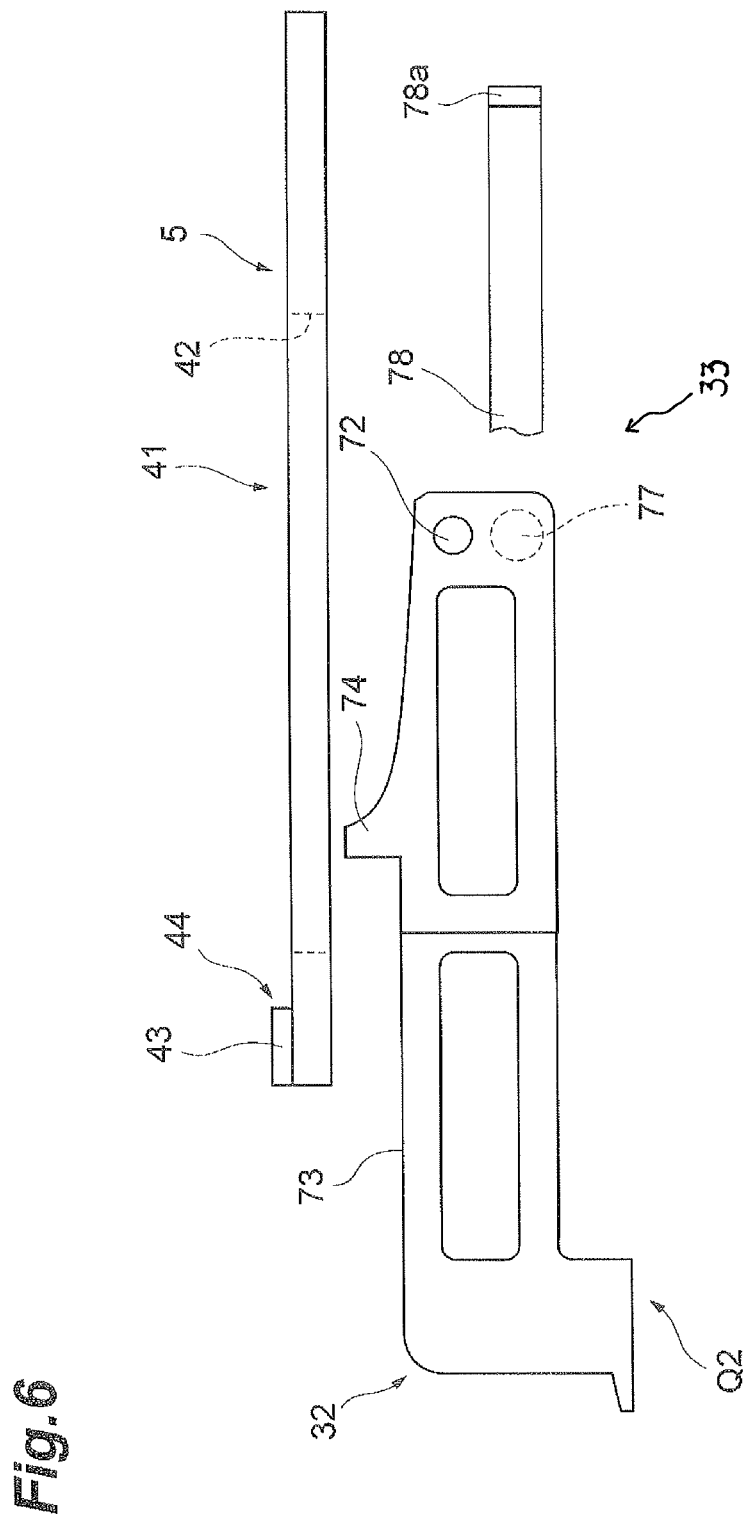
FIG. 6 is a side view showing the configuration of the receiver.

FIG. 5 is a perspective view showing the configuration of the receiver. FIG. 6 is a side view thereof. As shown in FIGS. 5 and 6, the receiver 32 is of an approximately rectangular parallelepiped shape with the width slightly smaller than the width of the opening 42 of the stage 5 and is arranged at a lower position than the stage 5 and beside the first slider 34, corresponding to the insertion-removal position P1 The receiver 32 is arranged between a pair of platelike members 71, 71 fixed to a bottom portion of the device and the far-side side portions of the receiver 32 are journaled through a rotary shaft 72 on the platelike members 71, 71. The top surface of the receiver 32 is a receiving surface 73 for the sample retaining member 6. At the far-side end of the receiving surface 73, there is a receiving surface positioning portion 74 provided for setting the position of the sample retaining member 6 on the receiving surface 73.

A pedestal 75 to which the insertion-removal portion 7 is fixed is arranged, as shown in FIG. 5, in the vicinity of the receiver 32. The pedestal 75 is provided around the periphery of the receiver 32 so as to expose the receiver 32, and a housing 81 (cf. FIG. 10) forming the insertion-removal portion 7 is fixed to the top surface of the pedestal 75. The lever member 76 for driving the aforementioned clamp portion 51 is provided on the side portion of the pedestal 75 on the first slider 34 side. The lever member 76 extends from the side portion of the pedestal 75 toward the far side and the tip portion 76a of the lever member 76 is outwardly obliquely bent toward the first slider 34 side. This tip portion 76a comes into contact with the pin 57 of the long-side clamp 52 with movement of the stage 5 to the insertion-removal position P1, to rotate the long-side clamp 52.

The receiver driving portion 33 is a portion that rotates the receiver 32 around the rotary shaft 72. The receiver driving portion 33 is composed of a pin 77 on the receiver 32 side and a lever member 78 on the stage 5 side. The pin 77 is fixed at a position below the rotary shaft 72 of the receiver 32 so as to project to the first slider 34 side, on the side of the receiver 32. A lever member 78, as shown in FIGS. 4 and 6, is provided on the bottom side of the stage 5. The lever member 78 extends along the first slider 34 on the bottom side of the stage 5, and a far-side end 78a of the lever member 78 is formed so as to be bent at an approximate right angle toward the receiver 32 side.

Figure 7:
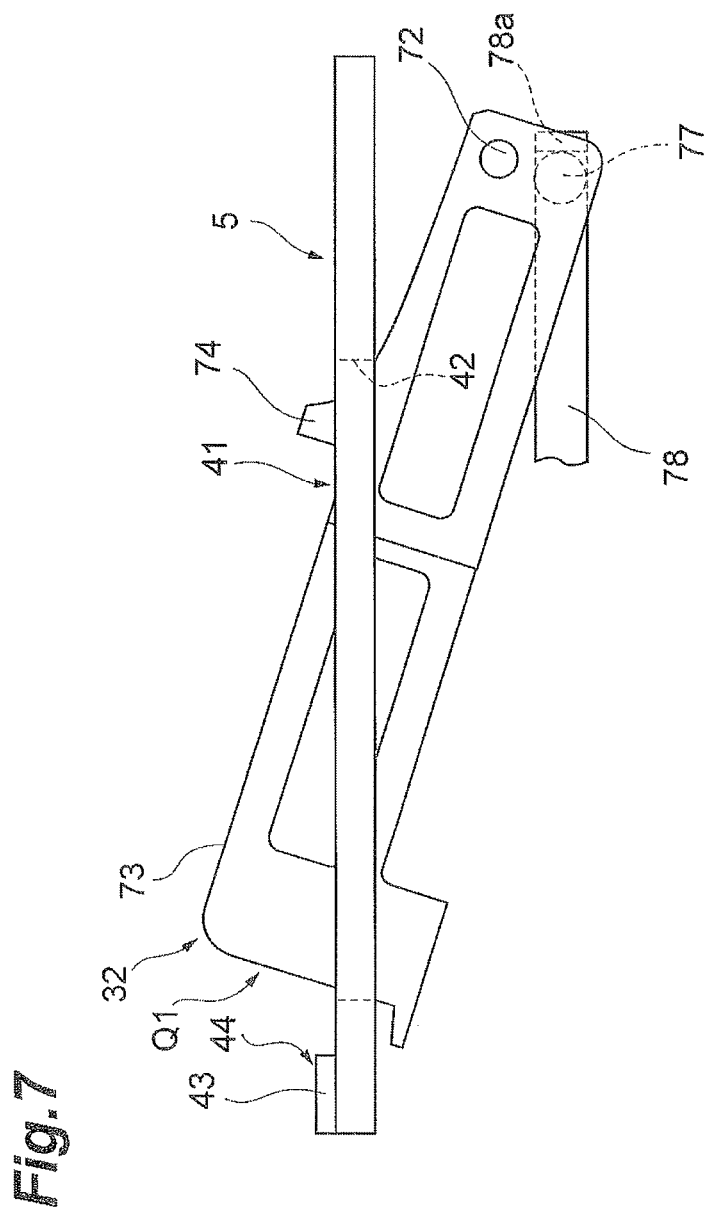
FIG. 7 is a side view showing a situation of driving of the receiver by a receiver driving unit.

As the stage 5 moves to the insertion-removal position P1, the end 78a of the lever member 78 comes into engagement with the pin 77 to push the pin 77 to the near side, as shown in FIG. 7. As the pin 77 is pushed, the receiver 32 is rotated around the rotary shaft 72 to move to an advance position Q1 where it projects out through the opening 42 of the stage 5 so that the receiving surface 73 makes a downward slope toward the receiving surface positioning portion 74. When the receiver 32 is located at the advance position Q1, an angle of inclination of the receiving surface 73 to the stage 5 is set, for example, to approximately 20° to 30°. As the stage 5 moves from the insertion-removal position P1 to the image acquisition position P2, the engagement between the end 78a of the lever member 78 and the pin 77 is released, whereby the receiver 32 moves to a retraction position Q2 where the receiving surface 73 is retracted from the opening 42 of the stage 5. When the receiver 32 is located at the retraction position Q2, the receiving surface 73 is kept approximately horizontal below the stage 5.

In the above embodiment the receiver driving unit 33 was composed of the pin 77 on the receiver 32 side and the lever member 78 on the stage 5 side, but the receiver driving unit does not have to be limited only to this mode. For example, a drive motor for driving the rotary shaft 72 may be provided on the receiver 32 so that the receiver 32 can be driven between the advance position Q1 and the retraction position Q2 in conjunction with movement of the stage 5 by the drive motor.

The following will describe the operation of the above-described insertion-removal mechanism 30 for the sample retaining member.

Figure 8:
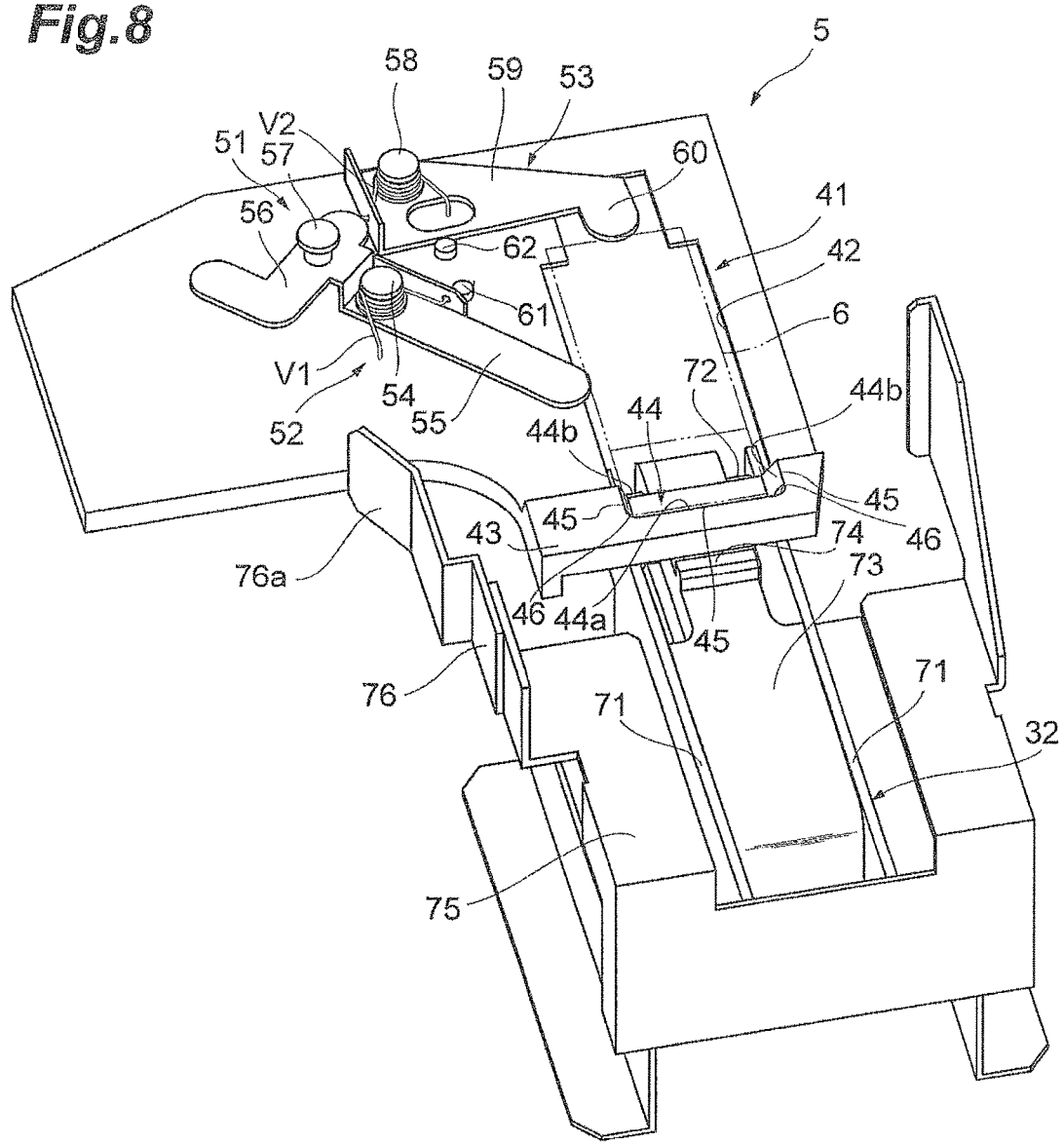
FIG. 8 is a perspective view showing an operation of the insertion-removal mechanism for the sample retaining member.
Figure 9:
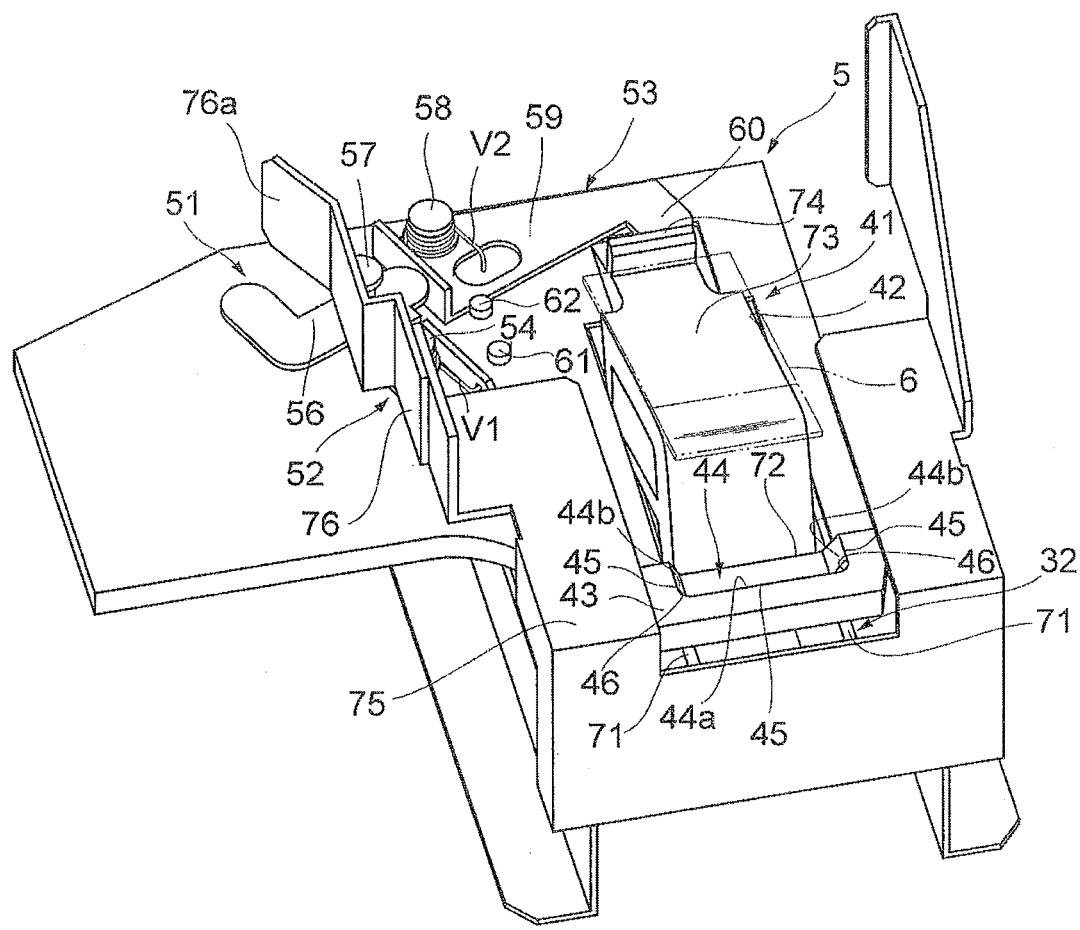
FIG. 9 is a perspective view showing an operation subsequent to FIG. 8.

When the stage 5 is located at the image acquisition position P2 side, the receiver 32 is kept as located at the retraction position Q2, as shown in FIG. 8. Furthermore, the clamp portion 51 is kept as located at the position where it holds the sample retaining member 6 on the mount surface 41. As the stage 5 moves to the insertion-removal position P1, the receiver driving unit 33 moves the receiver 32 to the advance position Q1 in conjunction with the movement of the stage 5, as shown in FIG. 9, whereby the receiving surface 73 comes to project out through the opening 42 of the stage 5. Furthermore, the clamp portion 51 moves to the position where the holding of the sample retaining member 6 is released, in conjunction with the movement of the stage 5.

Figure 10:
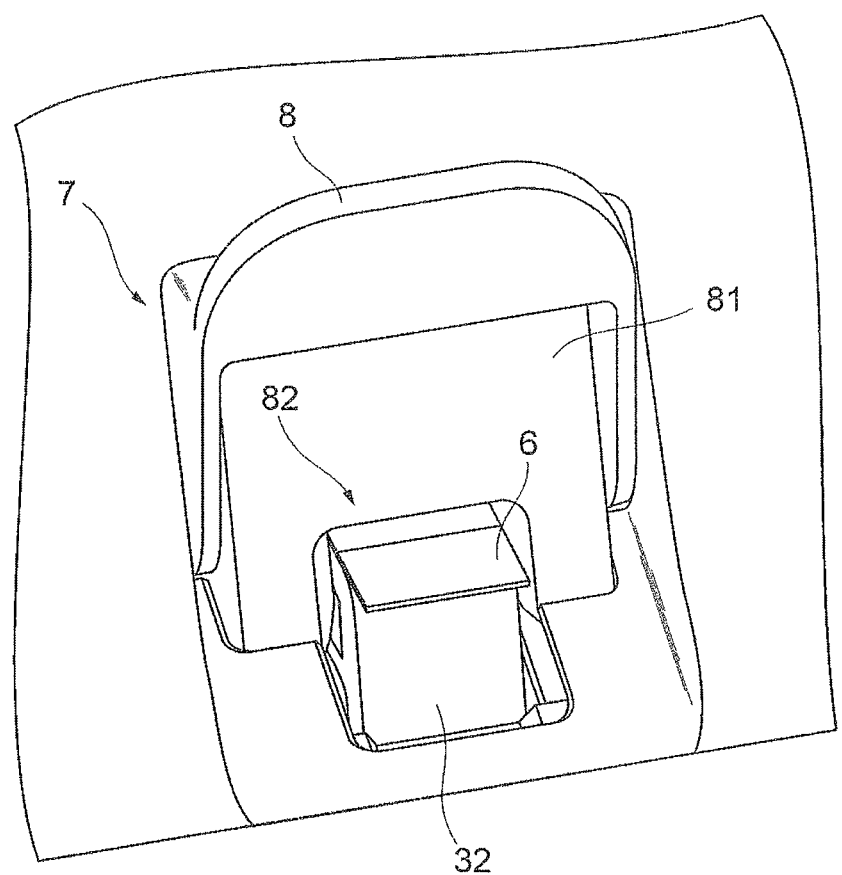
FIG. 10 is a perspective view showing a situation of an insertion-removal port in the state of FIG. 9.

At this time, as shown in FIG. 10, the receiver 32 is exposed in an inclined state from an insertion-removal port 82 when the open/close lid 8 is opened, in the insertion-removal portion 7. Therefore, when the sample retaining member 6 is put into the insertion-removal port 82, the sample retaining member 6 is mounted on the receiving surface 73 of the receiver 32 to be butted against the receiving surface positioning portion 74 by its own weight or by hand work. In removing the sample retaining member 6, the receiver 32 is moved to the advance position Q1 to transfer the sample retaining member 6 from the mount surface 41 of the stage 5 to the receiving surface 73, and then the sample retaining member 6 can be manually removed from the insertion-removal port 82.

Figure 11:
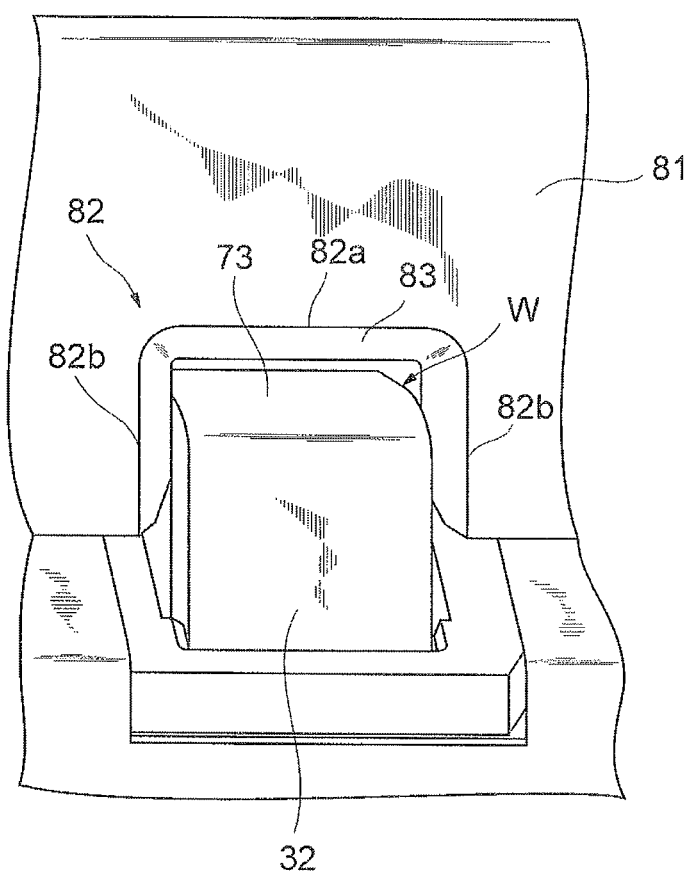
FIG. 11 is an enlarged front view of FIG. 10.

Here, as shown in FIG. 11, the insertion-removal port 82 is provided in the housing 81 forming the insertion-removal portion 7, so as to surround the receiving surface 73 and side portions of the receiver 32 having been moved to the advance position Q1. An upper wall portion 82a and side wall portions 82b, 82b forming the insertion-removal port 82 constitute a taper portion 83 such that the insertion-removal port 82 spreads out from the far side to the near side of the housing 81. In the insertion-removal port 82, a clearance W larger than the thickness of the sample retaining member 6 is present between the receiving surface 73 and the upper wall portion 82a when the receiver 32 is moved to the advance position Q1. The taper portion 83 and clearance W of this configuration facilitate the insertion and removal of the sample retaining member 6 into and from the insertion-removal port 82.

As the stage 5 is moved from the insertion-removal position P1 to the image acquisition position P2 with the sample retaining member 6 being butted against the receiving surface positioning portion 74, the receiver driving unit 33 moves the receiver 32 to the retraction position Q2 in conjunction with the movement of the stage 5, whereby the receiving surface 73 is retracted from the opening 42 of the stage 5 (cf. FIG. 8). Through this operation, the sample retaining member 6 is transferred from the receiving surface 73 to the mount surface 41 of the stage 5. Furthermore, the clamp portion 51 moves to the position where it holds the sample retaining member 6, in conjunction with the movement of the stage 5, whereby the sample retaining member 6 becomes positioned while butted against the mount surface positioning portion 44.

As described above, the insertion-removal mechanism 30 for the sample retaining member is configured so that at the insertion-removal position P1 of the sample retaining member 6 the receiver 32 is driven to the advance position Q1 by the receiver driving unit 33 to project out through the opening 42 of the stage 5 so that the receiving surface 73 makes the downward slope toward the receiving surface positioning portion 74. Because of this, the insertion-removal mechanism 30 for the sample retaining member can position the sample retaining member 6 by the receiving surface positioning portion 74 through the use of the downward slope of the receiving surface 73 by simply placing the sample retaining member 6 on the receiving surface 73, without need for positioning the sample retaining member 6 by hand work. After the positioning by the receiving surface positioning portion 74, the receiver 32 is driven to the retraction position Q2 by the receiver driving unit 33, whereby the sample retaining member 6 is transferred from the receiver 32 to the stage 5 so that the sample retaining member 6 can be readily and accurately arranged on the mount surface 41 of the stage 5.

In the insertion-removal mechanism 30 for the sample retaining member, the receiver driving unit 33 is composed of the pin 77 on the receiver 32 side and the lever member 78 on the stage 5 side and the movement of the receiver 32 between the advance position Q1 and the retraction position Q2 is switched in conjunction with the movement of the stage 5 between the insertion-removal position P1 and the image acquisition position P2 by the stage driving unit 31. Therefore, the convenience of the insertion-removal mechanism 30 can be improved.

In the insertion-removal mechanism 30 for the sample retaining member, the stage 5 has the mount surface positioning portion 44 for setting the position of the sample retaining member 6 on the mount surface 41 and the mount surface positioning portion 44 has the taper portion 45 widening to the end when viewed from the mount surface 41.

Since the mount surface positioning portion 44 is so formed, the positioning on the mount surface 41 of the stage 5 can be readily carried out. Since the mount surface positioning portion 44 has the taper portion 45, it can ensure the easiness of transfer in the operation of transferring the sample retaining member 6 from the receiver 32 to the stage 5. In the mount surface positioning portion 44, the stage 5 may be provided with a cut continuous to the opening 42 in order to prevent the wall from hitting the sample retaining member 6, but the configuration wherein the mount surface positioning portion 44 is composed of the thick part 43 and cut part as shown in FIG. 4 has the advantage that flatness in formation of the stage 5 can be readily ensured.

The stage 5 has the clamp portion 51 for butting the sample retaining member 6 against the mount surface positioning portion 44 in conjunction with the movement of the stage 5 from the insertion-removal position P1 to the image acquisition position P2 by the stage driving unit 31. This can prevent the sample retaining member 6 from suffering positional deviation during the movement of the stage 5 to the image acquisition position P2. Furthermore, the clamp portion 51 is configured so as to release the holding of the sample retaining member 6 in conjunction with the movement of the stage 5 from the image acquisition position P2 to the insertion-removal position P1 by the stage driving unit 31. Therefore, there is no hindrance to the transfer of the sample retaining member 6 between the stage 5 and the receiver 32 at the insertion-removal position P1.

In the insertion-removal mechanism 30 for the sample retaining member, the insertion-removal port 82 for the sample retaining member 6 is provided corresponding to the receiver 32 and the upper wall portion 82a and side wall portions 82b, 82b forming the insertion-removal port 82 have the taper portion 83 spreading out from the far side to the near side of the insertion-removal port 82. In the insertion-removal port 82, the clearance W larger than the thickness of the sample retaining member 6 is present between the receiving surface 73 and the upper wall portion 82a forming the insertion-removal port 82, when the receiver 32 is moved to the advance position Q1. This improves workability in placing the sample retaining member 6 on the receiver 32 or in removing the sample retaining member 6 from the receiver 32, through the insertion-removal port 82.

REFERENCE SIGNS LIST 1 image acquisition device; 5 stage; 6 sample retaining member; 11, 21 light sources; 12, 22 imaging devices; 30 insertion-removal mechanism for sample retaining member; 31 stage driving units; 32 receiver; 33 receiver driving unit; 41 mount surface; 42 opening; 44 mount surface positioning portion; 45 taper portion; 51 clamp portion; 73 receiving surface; 74 receiving surface positioning portion; 82 insertion-removal port; 82a upper wall portion (wall portion); 82b side wall portions (wall portions); 83 taper portion; P1 insertion-removal position; P2 image acquisition position; Q1 advance position; Q2 retraction position; S sample; W clearance.

The invention claimed is:
1. An insertion-removal mechanism for a sample retaining member to be used in an image acquisition device for acquiring an image of a sample, comprising:
 a stage having a mount surface for the sample retaining member to he mounted thereon, and an opening provided in the mount surface corresponding to a retaining region of the sample in the sample retaining member;

a stage driving unit for driving the stage between an insertion-removal position of the sample retaining member and an image acquisition position of the sample;

a receiver arranged at the insertion-removal position and having a receiving surface for the sample retaining member and a receiving surface positioning portion for setting a position of the sample retaining member on the receiving surface; and a receiver driving unit for driving the receiver between an advance position where the receiving surface projects out through the opening so as to make a downward slope toward the receiving surface positioning portion and a retraction position where the receiving surface is retracted from the opening, wherein the sample retaining member moves between the mount surface of the stage and the receiving surface of the receiver as the stag moves between the insertion-removal position and the image acquisition position.

2. The insertion-removal mechanism for the sample retaining member according to claim 1, wherein the receiver driving unit drives the receiver to the advance position in conjunction with movement of the stage from the image acquisition position to the insertion-removal position by the stage driving unit.

3. The insertion-removal mechanism for the sample retaining member according to claim 1, wherein the stage further has a mount surface positioning portion for setting a position of the sample retaining member on the mount surface, and wherein the mount surface positioning portion has a taper portion widening to the end when viewed from the mount surface.

4. The insertion-removal mechanism for the sample retaining member according to claim 3, wherein the stage further has a clamp portion for butting the sample retaining member against the mount surface positioning portion in conjunction with movement of the stage from the insertion-removal position to the image acquisition position by the stage driving unit.

5. The insertion-removal mechanism for the sample retaining member according to claim 1, wherein an insertion-removal port for the sample retaining member is provided corresponding to the receiver, and wherein a wall portion forming the insertion-removal port has a taper portion spreading out from the far side to the near side of the insertion-removal port.

6. The insertion-removal mechanism for the sample retaining member according to claim 5, wherein when the receiver is moved to the advance position, a clearance larger than a thickness of the sample retaining member is present between the receiving surface and the wall portion forming the insertion-removal port.

7. An image acquisition device comprising:

the insertion-removal mechanism for the sample retaining member as set forth in claim 1;

a light source for applying, light to the retaining region of the sample in the sample retaining member through the opening, when the stage is moved to the image acquisition position; and an imaging device for imaging a light figure of the sample formed by the light source.

\* \* \* \* \*